United States Patent [19]

Wermuth et al.

[11] Patent Number: 4,873,243

[45] Date of Patent: Oct. 10, 1989

[54] DERIVATIVES OF 3-IMINO-PYRIDAZINE, PROCESS FOR OBTAINING THEM AND PHARMACEUTICAL COMPOSITIONS CONTAINING THEM

[75] Inventors: Camille G. Wermuth, Strasbourg; Gilbert Schlewer, Ostwald; Michel Heaulme, Baillargues, all of France

[73] Assignee: SANOFI, Paris, France

[21] Appl. No.: 923,901

[22] Filed: Oct. 28, 1986

[30] Foreign Application Priority Data

Oct. 30, 1985 [FR] France .................. 85 16157

[51] Int. Cl.$^4$ .................. C07D 413/06; C07D 417/06; C07D 413/14; A61K 31/50
[52] U.S. Cl. .................. 514/248; 514/252; 514/254; 544/237; 544/238
[58] Field of Search .................. 514/248, 252, 254; 544/237, 238

[56] References Cited

U.S. PATENT DOCUMENTS 4,772,309 9/1988 Stetter et al. .................. 544/238

Primary Examiner—Mark L. Berch
Attorney, Agent, or Firm—Bacon & Thomas

[57] ABSTRACT

The invention relates to derivatives of 2,3-dihydro 3-imino-pyridazine responding to general formula:

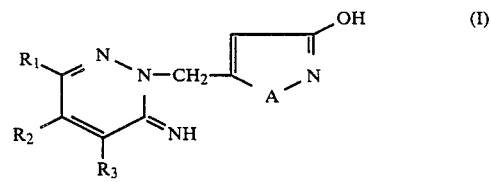

in which:
A represents an atom of oxygen or of sulfur;
$R_1$ represents a lower alkyl group, or an aromatic group selected from:
  the phenyl group;
  the phenyl groups mono- or poly-substituted by a halogen group, a lower alkyl group, a lower alkoxy group, a nitro group, a hydroxy or methylenedioxy group;
  the naphthyl group;
  the furyl group;
  the thienyl group or the pyridyl group;
$R_2$ and $R_3$ each designate independently hydrogen or a lower alkyl group; a phenyl group, or $R_2$ and $R_3$, taken together, constitute, with the 2 atoms of the pyridazinic cycle to which they are bonded, a benzene ring, and their pharmaceutically acceptable salts. Application: antidepressants or psychotonics.

6 Claims, No Drawings

DERIVATIVES OF 3-IMINO-PYRIDAZINE, PROCESS FOR OBTAINING THEM AND PHARMACEUTICAL COMPOSITIONS CONTAINING THEM

The present invention relates to novel derivatives of 2,3-dihydro-3-imino-pyridazine substituted on the nitrogen in 2 position by an isoxazolylmethyl group or an isothiazolylmethyl group.

The compounds according to the invention respond to the general formula:

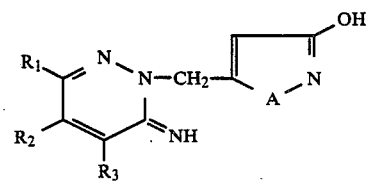

in which:
A represents an atom of oxygen or of sulfur;
$R_1$ represents a lower alkyl group, or an aromatic group selected from:
  the phenyl group;
  the phenyl groups mono- or poly-substituted by a halogen group, a lower alkyl group, a lower alkoxy group, a nitro group, a hydroxy or methylenedioxy group;
  the naphthyl group;
  the furyl group;
  the thienyl group or the pyridyl group;
$R_2$ and $R_3$ each designate independently hydrogen or a lower alkyl group; a phenyl group, or $R_2$ and $R_3$, taken together, constitute, with the 2 atoms of the pyridazinic cycle to which they are bonded, a benzene ring.

The salts formed by the compounds of formula (I) with the pharmaceutically acceptable acids form an integral part of the invention. A radiocrystallographic study made on the salts of the compounds of formula (I) shows that the double bond of the imino group is entirely delocalized. Consequently, the salts may exist in two tautomeric forms:

where $R_1$, $R_2$, $R_3$ and A are as defined hereinabove and XH represents an inorganic or organic acid, for example an halogenohydric acid.

These two tautomeric forms form part of the invention.

In the present Application, lower alkyl is understood to mean an alkyl group having from 1 to 4 carbon atoms. Lower alkoxy group is understood to mean a lower alkyl -O- group.

The compounds according to the invention may be prepared by action of a 3-methoxy-5-halogenomethyl isoxazole or isothiazole 2 on a suitably substituted 3-amino-pyridazine 1 in accordance with the reaction diagram:

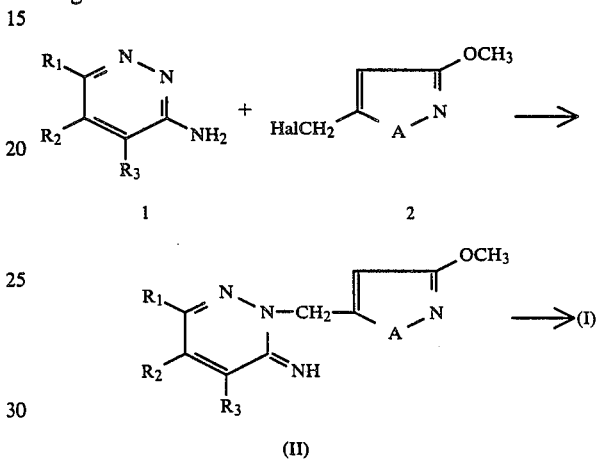

The O-methylated compounds (II) are thus obtained.

Reaction is carried out by heating the two reagents within a polar aprotic solvent, such as dimethylformamide, to a temperature of between 50° C. and the temperature of boiling of the solvent.

From products (II), compounds (I) are obtained by the conventional methods of dealkylation and in particular by the action of hydrobromic acid in acetic solution or by heating with pyridine hydrochloride.

The methylated compounds (II) are novel and are the key intermediates of the preparation of compounds (I). In this respect, they form an integral part of the invention, as well as their acid addition salts which may exist

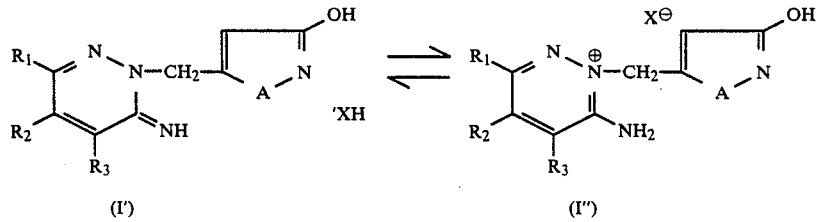

in the two tautomeric forms:

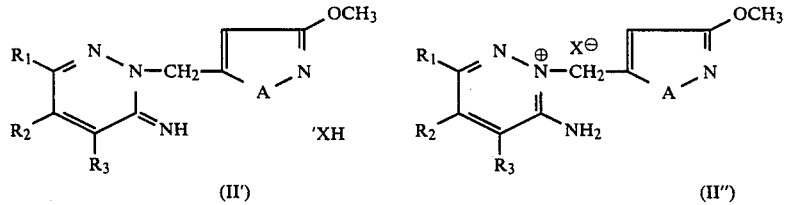

in which $R_1$, $R_2$, $R_3$ and A are as defined hereinabove and X represents the anion of an inorganic or organic acid.

The starting 3-amino pyridazines 1 are known and may be prepared from the corresponding 3-chloropyridazines, for example by action of the hydrazine which leads to the corresponding 3-hydrazino derivatives. These latter, by catalytic hydrogenation in the presence of Raney nickel, lead to compounds 1.

The 3-methoxy-chloro-(or bromo)-5-methyl-isoxazoles 2 are obtained from the 3-methoxy-5-hydroxymethylisoxazole by action respectively of the thionyl chloride or a brominated derivative of phosphorus such as $PBr_3$.

3-methoxy-5-hydroxymethyl-isoxazole is a known compound which may be prepared in accordance with the method indicated in Acta Chemica Scandinavia Series B 1976, B 30 (3), 281–2.

3-methoxy-5-chloromethyl-isothiazole is a known compound which may be prepared in accordance with the method described in the Journal of the American Chemical Society 65, 1569, (1943).

The following Examples will enable the invention to be more readily understood, without limiting the scope thereof. In these Examples, the compounds are designated by Applicants' in-house references.

EXAMPLE 1

2-[(3-hydroxy 5-isoxazolyl) methyl]-3-imino-4-methyl-6-phenyl-2,3-dihydro-pyridazine, hydrobromide (SR 95538)

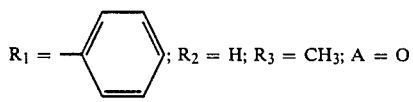

(I)

(a) 5-chloromethyl-3-methoxy-isoxazole

The mixture of 12.05 g of 5-hydroxymethyl-3-methoxy-isoxazole and 43 g of thionylchloride is heated to reflux for 30 minutes. After cooling, the reaction mixture is poured slowly over crushed ice and is extracted with ether. The organic phase is separated, washed with water and the solution is dried over magnesium sulfate. The solvent is evaporated then distilled in vacuo. 9.64 g of the expected product are obtained.

b.p. 0.2 mm of Hg=30° C.;
yield: 70%.

(b) 3-imino-2-[(3-methoxy-5-isoxazolyl) methyl] 4-methyl-6-phenyl-2,3-dihydro-pyridazine To the solution of 1.85 g of 3-amino-4-methyl-6-phenyl-pyridazine in 10 ml of dimethylformamide, are added 1.62 g of 5-chloromethyl-3-methoxy-isoxazole, then the product is heated to 80° C. for 4 hours.

After cooling, a saturated solution of sodium bicarbonate is added and the product is extracted with ethyl acetate. The organic phase is separated, washed with salt water, then the solution is dried over magnesium sulfate. The solvent is evaporated in vacuo. The crude product is chromatographed over silica column and, by eluting with ethyl acetate, the expected product is obtained (1.77 g) in the form of an oil. Yield: 60%.

By action of gaseous hydrochloric acid, the product is converted into its hydrochloride. m.p.=240° C. with decomposition.

(c) SR 95538

1.5 g of the product obtained hereinabove in the form of base are heated to 100° C. for 4 hours in 15 ml of a 48% (50/50 vol/vol) acetic acid/hydrobromic acid mixture. After concentration to a small volume, 1.2 g of the expected product separate. The hydrobromide crystallizes with 0.5 molecule of water.

m.p.=164° C. with decomposition;
Yield: 65%

EXAMPLE 2

2-[(3-hydroxy-5-isothiazolyl)methyl]-3-imino-6-(4-chloro-phenyl)-2,3-dihydro-pyridazine, hydrobromide (SR 95885)

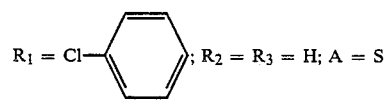

(I)

(a) 2-[(3-methoxy-5-isothiazolyl) methyl]-3-imino-6-(4-chloro-phenyl)-2,3-dihydro-pyridazine, hydrochloride The mixture of 0.500 g of 3-amino-6-(4-chloro-phenyl)-pyridazine and 0.438 g of 5-chloromethylene-3-methoxy-isothiazole in 10 ml of dimethylformamide is heated under argon at 80° C. for 14 hours.

After cooling, the precipitate is drained and washed with acetone. The product is recrystallized from ethanol. Colourless flakes are obtained.

m.p.=226° C.;
Weight=0.480 g;
Yield: 53%.

(b) SR 95885

The base of the hydrochloride obtained hereinabove is released by neutralization with normal sodium hydroxide and extraction with dichloromethane. The solution is dried and the solvent is evaporated.

The solution of 0.400 g of the base in 20 ml of 48% (50/50 vol/vol) acetic acid/hydrobromic acid mixture is heated to 100° C. for 3 hours.

The product is evaporated to dryness in vacuo and the residue is taken up in acetone. A colourless solid is obtained which is drained and recrystallized from ethanol.

m.p.=255° C.;
Weight=0.300 g
Yield: 46%

EXAMPLES 3 TO 8

By operating as in Example 2, but by varying the reagents, compounds I shown in Table hereinbelow are prepared.

In each case, the duration and temperature of heating used for demethylation in accordance with Example 2(b) have been indicated.

TABLE I

Structure: R1, R2, R3 substituted pyridazine with N-N-CH2-[A ring with OH, N]-NH group, HBr salt

| Code N° | R1 | R2 | R3 | A | m.p. °C. (1) | Demethylation: temperature duration | Ex N° |
|---|---|---|---|---|---|---|---|
| 95884 | phenyl | H | H | O | 202 | 100° C. - 12 h | 3 |
| 95812 | benzyl (–CH2–phenyl) | H | H | O | 220 | 100° C. - 6 h | 4 |
| 95895 | methylenedioxyphenyl | H | H | O | 240 | 100° C. - 3 h | 5 |
| 95886 | —CH3 | phenyl | H | S | 178 | 100° C. - 4 h | 6 |
| 95893 | thienyl | H | H | O | 220 | 80 h–2 h | 7 |
| 95894 | phenyl | —CH=CH—CH=CH | | O | 151 | 100° C. - 2 h 30 min | 8 |

(1) Melting point after recristallisation from ethanol.

The therapeutic activity of the products according to the invention has been studied. In order to demonstrate it, the neurochemical activity of the products on the GABA-ergic system has been studied, which was assessed by measuring the displacement of the gamma amino butyric acid (GABA) from its post-synaptic receptor.

The study was carried out in accordance with the method of ENNA and SNYDER (Brain Research 100, 81–97, 1975). The experiment was carried out in vitro in the presence of a suspension of synaptic membrane and tritiated GABA at a final concentration of 2.9 nM.

The results are expressed in Inhibit Concentration 50 (IC50), i.e. the micromolar concentration which inhibits 50% of the fixation of the GABA on its post-synaptic receptor.

The results obtained with various products of the invention are shown in Table 2.

TABLE 2

| Product SR Code No. | Example No. | IC50 in micromoles |
|---|---|---|
| 95538 | 1 | 1 |
| 95885 | 2 | 0.15 |
| 95884 | 3 | 1.8 |
| 95812 | 4 | 1.2 |
| 95895 | 5 | 0.075 |
| 95886 | 6 | 6.6 |
| 95893 | 7 | 1.6 |
| 95894 | 8 | 0.12 |

The products according to the invention therefore act on the neurone by occupation of the receptor site of the gamma amino butyric acid.

Due to their neurochemical properties, their use can therefore envisaged in human therapeutics and in particular as antidepressants or psychotonics.

The anti-depressant properties of the products according to the invention have been studied in the animal. The anti-depressant activity was assessed in the test of antagonism of reserpine-induced ptosis in the mouse.

The study was carried out on batches of 10 female mice weighing 20±1 g. The products to be studied were administered by the intraperitoneal route at the same time as the reserpine by the intravenous route at the dose of 2 mg/kg.

In parallel, a control batch received only the vehicle of administration of the product to be studied and the reserpine.

One hour after administration, the animals were observed individually. All the animals of the control batch presented ptosis. For the treated batches, the animals not presenting ptosis were counted and the percentage of the animals where the ptosis was antagonized were determined.

At the dose of 100 mg/kg by the intraperitoneal route, compound SR 95538 inhibits ptosis in 30% of the animals.

Furthermore, the products according to the invention do not present any marked toxicity at the doses where they are active. Product SR 95538 (Example 1) shows no sign of acute toxicity in the mouse at the dose of 100 mg/kg by the intraperitoneal route. The products according to the invention may be administered by the oral route or by the injectable route.

The pharmaceutical compositions may be solid or liquid and can be presented for example in the form of tablets, gelatine capsules, granules or injectable preparation.

Dosage may vary within wide limits depending on the type and seriousness of the disorder to be treated and depending on the mode of administration. When administered orally to adults, it is most frequently between 0.010 g and 0.500 g per day, possibly divided up into several doses.

The following galenic preparation may be indicated by way of example:

| Gelatine capsules | |
|---|---|
| Product of Example 1 | 50 mg |
| Aerosil | 0.5 mg |
| Magnesium stearate | 1.5 mg |
| Starch STA X 1500 | 48 mg |
| | 100 mg |

Furthermore, as the products according to the invention are powerful selective GABA A antagonists, they may be used as biological reagents, in particular for studying the biological systems where a GABA-ergic mechanism is likely to intervene.

Finally, it is known that, for different classes of insecticides, a mechanism of action as inhibitor of the GABA A receptor has been demonstrated. Reference may be made in particular to the article by L. J. LAWRENCE and J. E. CASSIDA, Life Science 35, 171, 1984 on this subject. As powerful antagonists of the GABA A receptor, the products according to the invention present an insecticidal activity.

What is claimed is:

1. Derivatives of 3-imino-2,3-dihydro-pyridazines, having the formula:

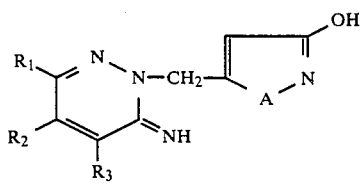
(I)

in which:
A represents an atom of oxygen or of sulfur;
$R_1$ represents a $C_1$–$C_4$ alkyl group, or an aromatic group selected from:
the phenyl group;
the phenyl group which is mono- or poly-substituted by halogen group, a $C_1$–$C_4$ alkyl group, a $C_1$–$C_4$ alkoxy group, a nitro group, a hydroxy or methylene-dioxy group;
the napththyl group;
the furyl group;
the thienyl group or the pyridyl group;
$R_2$ and $R_3$ each designate independently hydrogen or a lower alkyl group; a phenyl group, or $R_2$ and $R_3$, taken together, constitute, with the 2 atoms of the pyridazinic cycle to which they are bonded, a benzene ring; and the addition salts of these compounds, with pharmaceutically acceptable acids, corresponding to formulae I' or I":

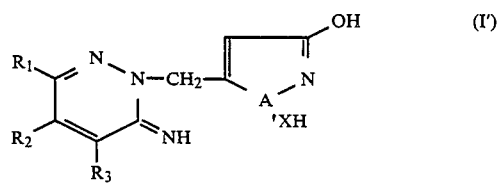
(I')

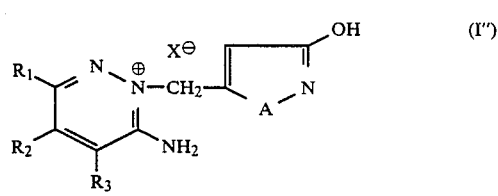
(I")

in which $R_1$, $R_2$, $R_3$ and A are defined hereinabove and X represents the anion of an acid.

2. The derivatives of claim 1, wherein $R_1$ is an aromatic group, $R_2$ and $R_3$ represent hydrogen.

3. The derivatives of claim 1, wherein $R_1$ is a $C_1$–$C_4$ alkyl, $R_2$ is the phenyl group and $R_3$ is hydrogen.

4. The derivatives of claim 1 wherein they are in the form of halohydric acid salts.

5. Derivatives of 3-imino-2,3-dihydro-pyridazines, which have the formula:

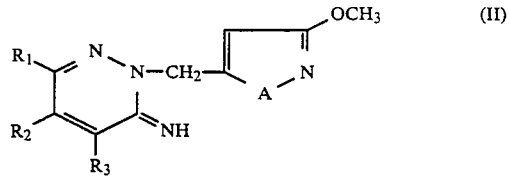
(II)

in which:
A represents an atom of oxygen or of sulfur;
$R_1$ represents a $C_1$–$C_4$ alkyl group, or an aromatic group selected from:
the phenyl group;
the phenyl group which is mono- or polysubstituted by a halogen group, a $C_1$–$C_4$ alkyl group, a $C_1$–$C_4$ alkoxy group, a nitro group, a hydroxy or methylene-dioxy group;
the naphthyl group;
the furyl group;
the thienyl group or the pyridyl group;
$R_2$ and $R_3$ each designate independently hydrogen or a lower alkyl group; a phenyl group, or $R_2$ and $R_3$, taken together, constitute, with the 2 atoms of the pyridazinic cycle to which they are bonded, a benzene ring; and the addition salts of these compounds of formulae:

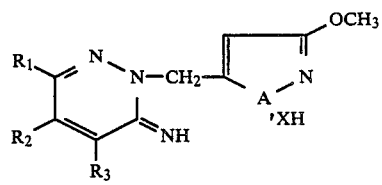

(II')

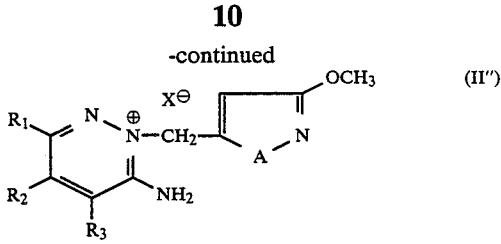

(II")

in which $R_1$, $R_2$, $R_3$ and A are as defined hereinabove and X represents the anion of a pharmaceutically acceptable acid.

6. A pharmaceutical composition having anti-depressant action, wherein said composition contains an effective amount of a derivative of 3-imino-2,3-dihydropyridazine according to claim 1 in combination with a carrier.

* * * * *